United States Patent [19]
Dolak et al.

[11] Patent Number: 4,473,649
[45] Date of Patent: Sep. 25, 1984

[54] ANTIBIOTIC PRODUCING STREPTOMYCES

[75] Inventors: Lester A. Dolak, Cooper Township, Kalamazoo County; Fritz Reusser, Portage; Thomas M. Castle, Cooper Township, Kalamazoo County; Betty R. Hannon, Kalamazoo Township, Kalamazoo County; Alice L. Laborde, Kalamazoo; Charles K. Marschke, Portage, all of Mich.

[73] Assignee: The Upjohn Company, Kalamazoo, Mich.

[21] Appl. No.: 414,239

[22] Filed: Sep. 2, 1982

Related U.S. Application Data

[62] Division of Ser. No. 341,437, Jan. 22, 1982, Pat. No. 4,404,190.

[51] Int. Cl.$^3$ .......................... C12N 1/20; C12R 1/465
[52] U.S. Cl. .................................... 435/253; 435/886
[58] Field of Search ................................ 435/253, 886

[56] References Cited
PUBLICATIONS

ATCC Catalogue of Strains I 15 Ed., p. 228 (1982).

*Primary Examiner*—Alvin E. Tanenholtz
*Attorney, Agent, or Firm*—Roman Saliwanchik; Joan Thierstein

[57] ABSTRACT

Novel antibiotic U-64,864 producible in a fermentation under controlled conditions using a biologically pure culture of the microorganism *Streptomyces braegensis* Dietz sp.n., NRRL 12567. This antibiotic is active against various Gram-positive bacteria, for example, *Staphylococcus aureus*, *Streptococcus pyogenes* and *Streptococcus pneumoniae*. Thus, antibiotic U-64,864 can be used in various environments to eradicate or control such bacteria.

1 Claim, 5 Drawing Figures

FIGURE A
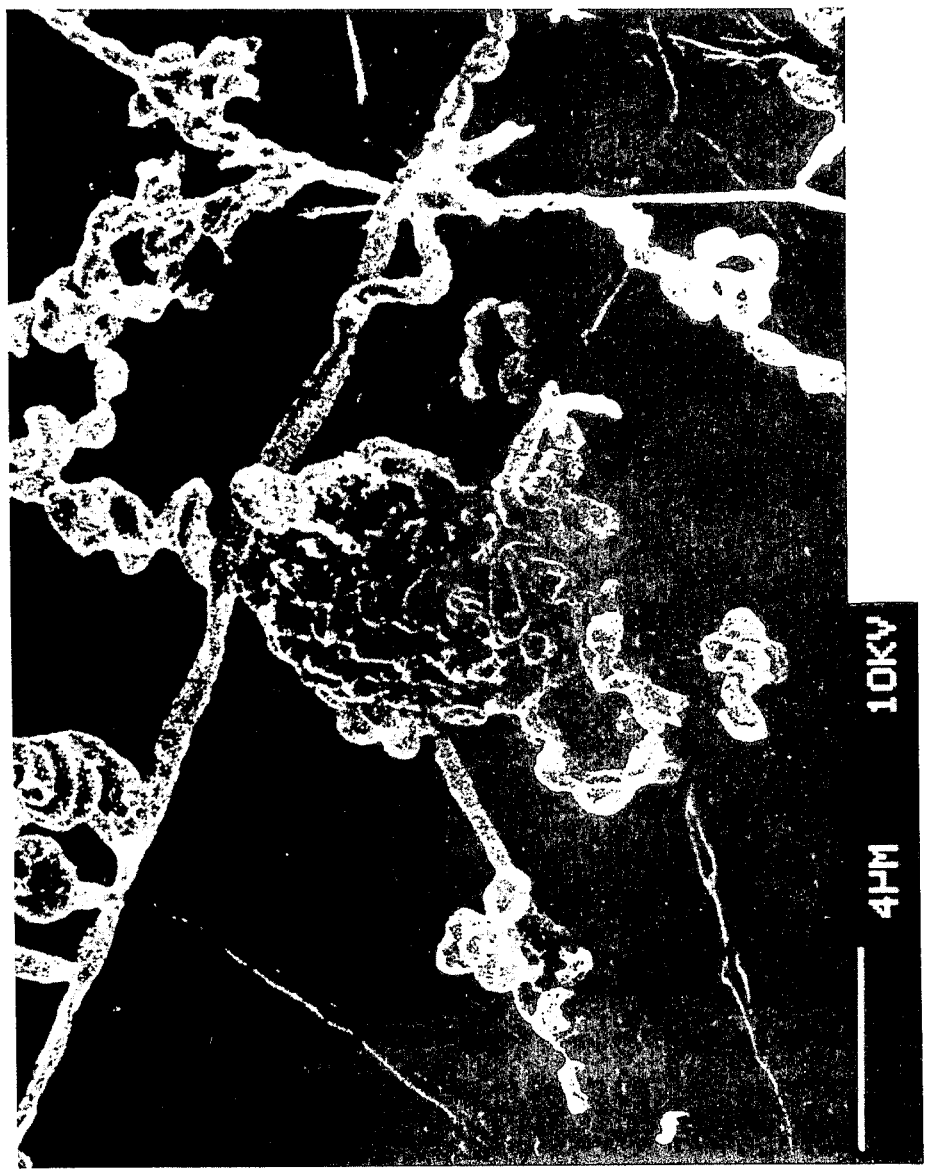

ANTIBIOTIC PRODUCING STREPTOMYCES

This is a division of application Ser. No. 341,437, filed Jan. 22, 1982, now U.S. Pat. No. 4,404,190.

DESCRIPTION

BRIEF SUMMARY OF THE INVENTION

Antibiotic U-64,864 is producible in a fermentation under controlled conditions using a biologically pure culture of the new microorganism *Streptomyces braegensis* Dietz ap.n., NRRL 12567.

Antibiotic U-64,864 is an acidic compound which is active against various Gram-positive bacteria. Thus antibiotic U-64,864 can be used to disinfect washed and stacked food utensils contaminated with *S. aureus*. It can also be used as a disinfectant on various dental and medical equipment contaiminated with *S. aureus*. Still further, antibiotic U-64,864 can be used as a bacteriostatic rinse for laundered clothes, and for impregnating papers and fabrics; and it is also useful for suppressing the growth of sensitive organisms in plate assays and other microbiological media.

DETAILED DESCRIPTION OF THE INVENTION

Chemical and Physical Properties of Antibiotic U-64,864:

Molecular Weight: 468 (mass spectrometry)
Molecular Formula: $C_{18}H_{35}ClN_4O_9$
Color of Pure Solid: White
Ultraviolet Absorption Spectrum:

The UV spectrum of antibiotic U-64,864 is shown in FIG. 2 of the drawings. At 0.1 mg/ml in 1:1 methanol:water the spectra are as follows:

Neutral: $\lambda max = 290 + 225$ sh
Base: $\lambda max = 302 + 235$
Acid: $\lambda max = 295$ Elemental Composition: C, 46.55; H, 5.95; N, 10.22; Cl, 6.60.

Melting Point: >350°.

Infrared Absorption Spectrum: Antibiotic U-64,864 has a characteristic infrared absorption spectrum when pressed into a KBr pellet as shown in FIG. 1 of the drawings. Peaks are observed at the following wavelengths.

| Band Freq.[1] | Inten[2] | Type[3] | Band Freq. | Inten. | Type |
|---|---|---|---|---|---|
| 3391.2 | 6 | BRD | 1235.5 | 28 | BRD |
| 3283.2 | 7 | BRD | 1209.5 | 28 | BRD |
| 2961.0 | 16 | BRD | 1157.4 | 31 | BRD |
| 2938.9 | 15 | BRD | 1129.4 | 32 | BRD |
| 2880.0 | 21 | SH | 1056.1 | 23 | AVG |
| 2668.8 | 42 | SH | 1033.0 | 31 | SH |
| 2105.5 | 70 | BRD | 956.8 | 50 | SH |
| 1649.3 | 3 | BRD | 906.6 | 50 | BRD |
| 1580.8 | 6 | BRD | 837.2 | 42 | AVG |
| 1459.3 | 19 | BRD | 779.3 | 38 | SH |
| 1422.6 | 17 | BRD | 734.9 | 34 | BRD |
| 1384.0 | 9 | AVG | 679.9 | 30 | BRD |
| 1321.3 | 19 | AVG | 622.1 | 27 | AVG |
| 1281.8 | 26 | BRD | | | |

[1] Wave numbers (cm$^{-1}$)
[2] Percent transmittance (% T);
[3] SH = shoulder
AVG = average
BRD = broad
SHP = sharp
Intensity at 4000 cm$^{-1}$ is 73% T.

C-Nuclear Magnetic Resonance (NMR) Spectrum

The $^{13}$C-NMR spectrum of antibiotic U-64,864 is shown in FIG. 3 of the drawings. The $^{13}$C-NMR spectrum was observed on a Varian CFT-80 Spectrometer on a solution (ca. 0.5 ml., ca. 200 mg/ml) of the sample of the antibiotic in deuterium oxide (D$_2$O). The spectrum was calibrated against external tetramethylsilane and frequencies were recorded in ppm downfield from tetramethylsilane.

Proton Magnetic Resonance ($^1$H-NMR) Spectrum

The $^1$H-NMR spectrum of antibiotic U-60,394 at 100 MHZ is shown in FIG. 4 of the drawings. The $^1$H-NMR spectrum was observed on a Varian XL-100-15 Spectrometer on a solution (ca. 0.5 ml., ca. 150 mg/ml) of the sample of the antibiotic in deuterium oxide (D$_2$O). The spectrum was calibrated against external tetramethylsilane and frequencies were recorded in ppm downfield from tetramethylsilane.

Solubilities

Antibiotic U-64,864 is highly siluble in water and water miscible solvents.

Antimicrobial Spectrum of Antibiotic U-64,864

Antibiotic U-64,864 is active against various Gram-positive bacteria as shown in the following tables.

Assay

The antibacterial assay is a standard agar dilution assay. The MIC is determined by standard methods using two-fold dilutions of the antibiotic in Brain Heart Infusion Broth (Difco Lab., Detroit, Mich.). One hundred μl of these dilutions are applied to ½ inch filter paper discs and spotted on agar plates seeded with the test organisms. The plates are incubated overnight at 31° C. and the read. The lowest concentration still yielding a distinct zone of inhibition is considered the MIC for that test organism.

| Microorganism | | Minimum Inhibitory Concentration (mcg/ml) |
|---|---|---|
| *Staphyloccus aureus* | UC 76 | 1000 |
| *Staphylococcus aureus* | UC 6685 | 500 |
| *Streptococcus pyogenes* | UC 152 | 31.2 |
| *Streptococcus pneumoniae* | UC 41 | 31.2 |
| *Streptococcus faecalis* | UC 694 | >1000 |
| *Escherichia coli* | UC 45 | >1000 |
| *Klebsiella pneumoniae* | UC 58 | >1000 |
| *Salmonella schottmuelleri* | UC 126 | >1000 |
| *Pseudomonas aeruginosa* | UC 95 | >1000 |

"UC" is a registered trademark of the Upjohn Company Culture Collection. These cultures can be obtained from The Upjohn Company in Kalamazoo, Mich., upon request.

Figure 1:
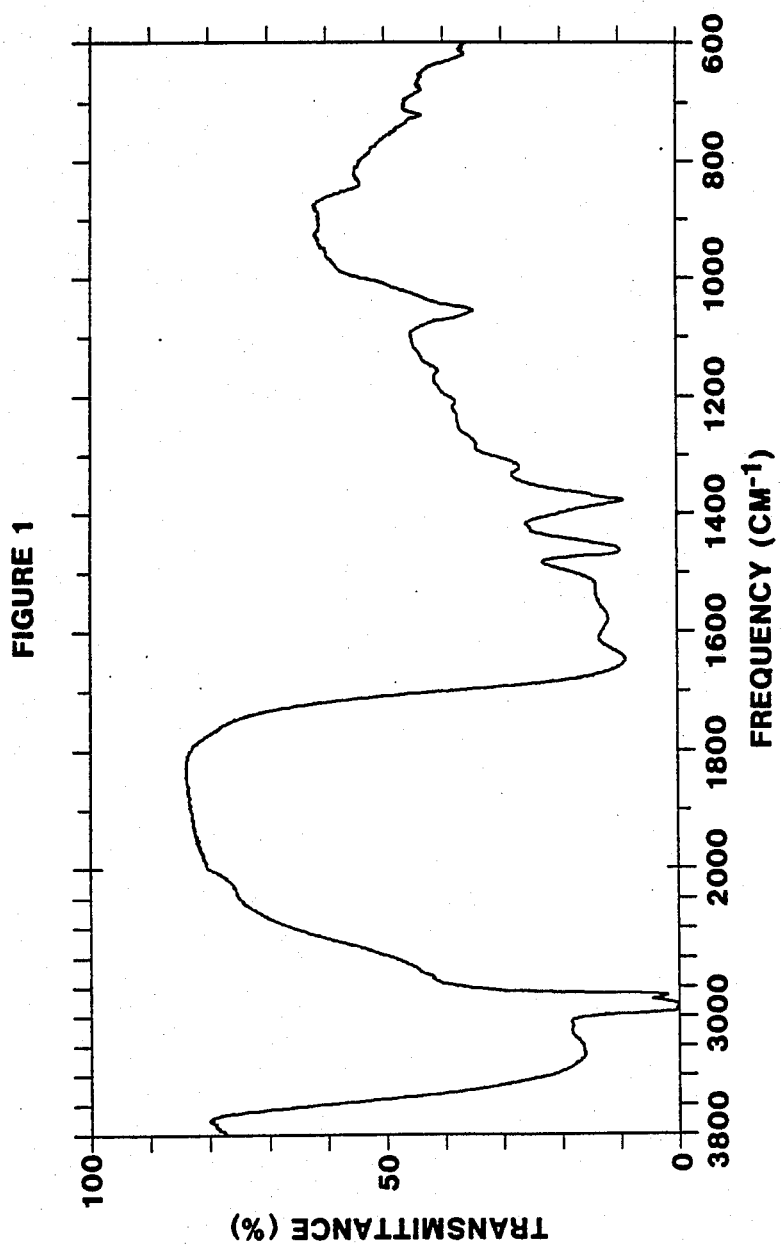
FIG. 1—Infrared absorption spectrum of antibiotic U-64,864.
Figure 2:
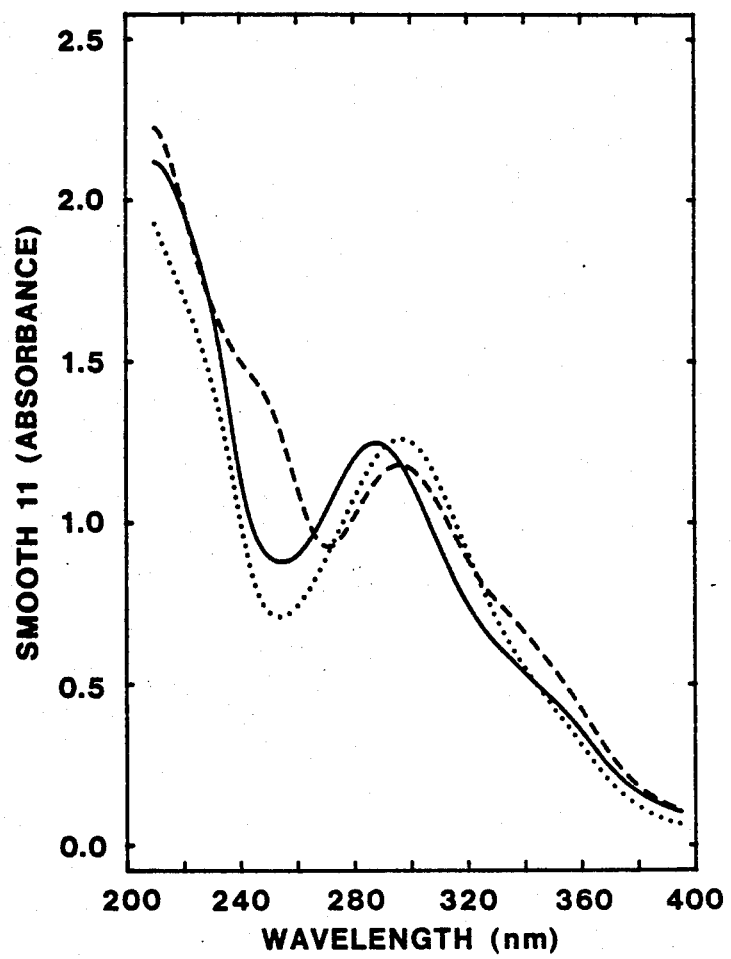
FIG. 2—UV spectrum of antibiotic U-64,864.
Figure 3:
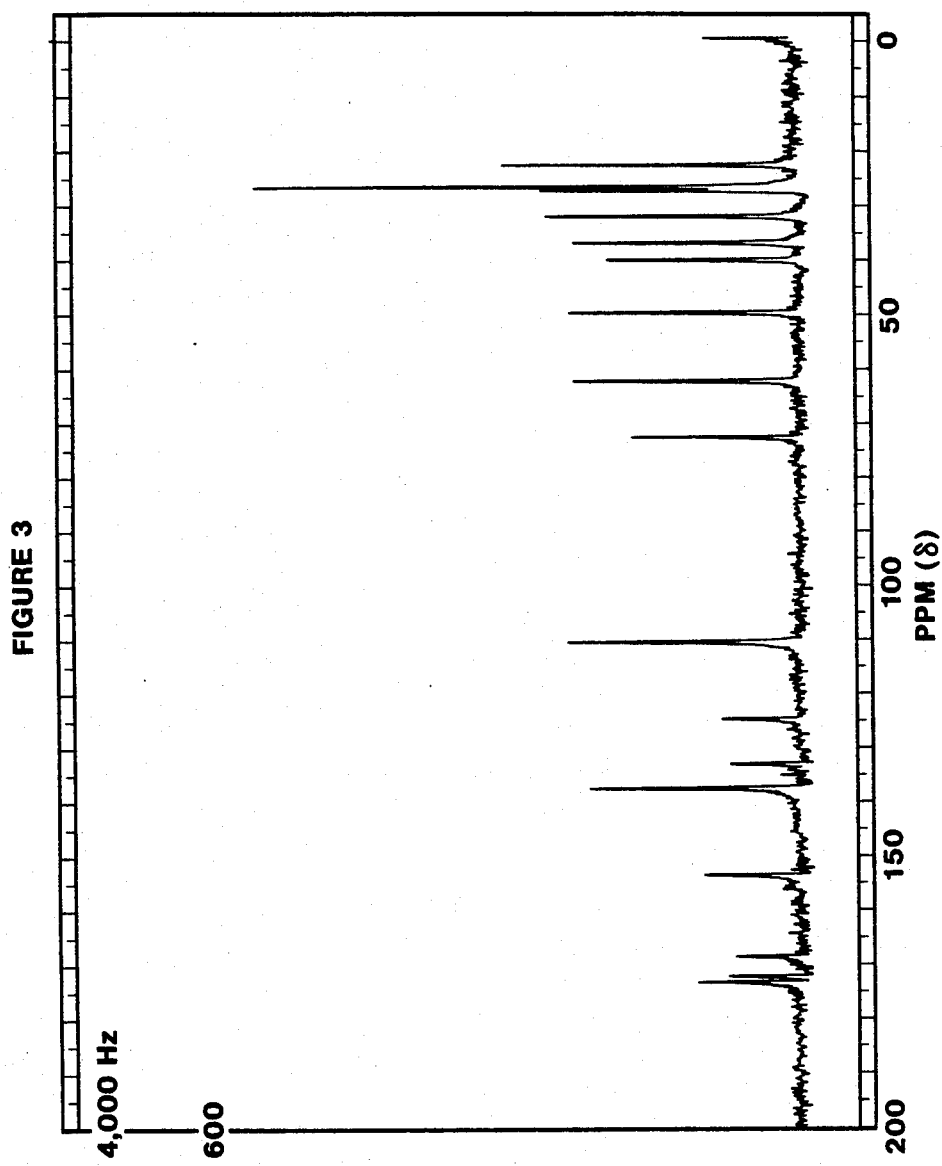
FIG. 3—$^{13}$C-Nuclear Magnetic Resonance (NMR) spectrum of antiobiotic U-64,864.
Figure 4:
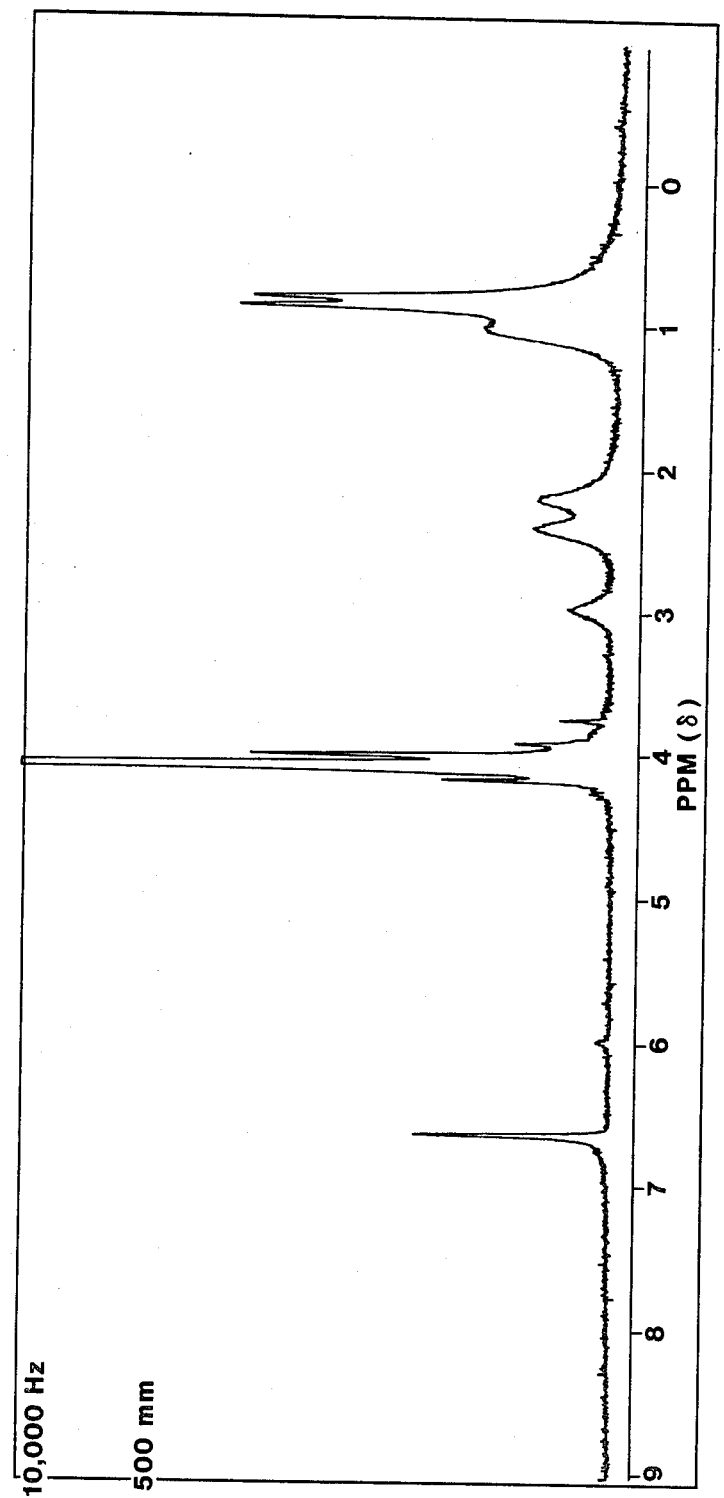
FIG. 4—Proton Magnetic Resonance ($^1$H-NMR) spectrum of antibiotic U-64,864.

FIG. A—Scanning electron micrograph of spores and spore structures of *Streptomyces braegensis*, Diets sp. nov., NRRL 12567.

THE MICROORGANISM

The microorganism used for the production of antibiotic U-64,864 is a biologically pure culture of *Streptomyces braegensis*, Dietz sp.n, NRRL 12567.

A subculture of this microorganism can be obtained from the permanent collection of the Northern Regional Research Laboratory, U.S. Department of Agriculture, Peoria, Ill., U.S.A. A viable subculture was deposited on Nov. 2, 1981. Its accession number in this depository is NRRL 12567. It should be understood that the availability of the culture does not constitute a license to practice the invention in derogation of patent rights granted with the subject instrument by governmental action.

The microorgansim of this invention was studied and characterized by Alma Diets of The Upjohn Research Laboratories.

*Streptomyces braegensis*, Dietz sp. nov., NRRL 12567.

Color Characteristics: Aerial mycelium predominantly gray. Melanin-negative. The color pattern on Ektachrome is given in Table 1. Reference color characteristics are given in Table 2. The culture may be placed in the Gray (GY) color series of Tresner and Backus [Tresner, H. D. and E. J. Backus. 1963. System of color wheels for streptomycete taxonomy. Appl. Microbiol. 11:335–338].

Microscopic Characteristics: Tight spiral spore chains are observed by phase-contrast microscopy. Many of the clains appear to be in hygroscopic masses. The masses show a unique brain-like appearance by Scanning Electron Microscopy. The spores in the masses look like red blood cells. Other spores have a hat-shaped appearance. All are smooth-surfaced and measure 1.0×0.6 μm. There is some indication of development of rectangular smooth-surfaced spores in the substrate mycelium. Fourteen-day cover glass preparations were used for the microscopic examinations.

Growth on Carbon Compounds: See Table 3.

Whole Cell Analysis: L-diaminopimelic acid was detected.

Culture Characteristics- General: See Table 4.

Temperature: The culture grew at 18°–37° C. on Bennett's, Czapek's sucrose, and maltose-tryptone agars. Optimum growth was at 24°–28° C.

Antibiotic U-64,864 is produced.

Source: Soil sample from Belize.

Type Strain: *Streptomyces braegensis* sp. nov., NRRL 12567.

*S. braegensis*, NRRL 12567 appeared most similar on Ektachrome (Table 1) to *Streptomyces vinaceus-drappus*, (NRRL-2363) which is described in Shirling and Gottlieb [Shirling, E. B. and D. Gottlieb. 1969. Cooperative description of type cultures of Streptomyces IV. Species descriptions from second, third and fourth studies. Int. J. Syst. Bacteriol. 19:391–512] and Bergy's Manual 8th ed. [Pridham, T. G., and H. D. Tresner. 1974. Part 17. Actinomycetes and related organisms. Family VII. Streptomycetaceae Waksman and Henrici 1943. Genus I. Streptomyces Waksman and Henrici 1943. Table 17.44f of the Gray series. Pages 814, 817, 818 in Buchman and Gibbons, eds., Bergy's Manual of Determinative Bacteriology, 8th ed. The Willams and Wilkins Co., Baltimore] and cited in Skerman et al [Skerman, V. B. D., V. Mcgowan, and P. H. A. Sneath. 1980. Approved Lists of Bacterial Names. Int. J. Syst. Bacteriol. 30:225–420]. Both cultures have spiral chains of smooth surfaced spores. The new culture has tightly coiled chains; *S. vinaceus-drappus* has long chains which are loosely coiled. Many of the spore chains of *Streptomyces braegensis*, NRRL 12567 appear to be in hygroscopic masses when observed with the phase-contrast microscope. The masses have a unique brain-like appearance when observed with the scanning electron microscope (see FIG. A). The uniqueness of the cells is detailed in the section "Microscopic Characteristics." Both cultures are malanin-negative. *Streptomyces braegensis*, NRRL 12567 belongs to the Gray (GY) series of Tresner and Backus [Tresner, H. D. and E. J. Backus. 1963. System of color wheels for streptomycete taxonomy. Appl. Microbiol. 11:335-338.]; *S. vinoceus-drappus* belongs to the Red (R) series. The cultures are further differentiated by their Reference Color Characteristics (Table 2); Growth on Carbon Compounds in the Synthetic Medium of Shirling and Gottlieb (Table 3) and General Cultural Characteristics (Table 4). *Streptomyces braegensis*, NRRL 12567 does not grow at 45° C.; *S. vinaceus-drappus* grows well at 45° C. The characteristics of the cultures are sufficiently different to warrant the designation of *Streptomyces braegensis*, NRRL 12567 as a new streptomycete species. Therefore, the culture is designated *Streptomyces braegensis* sp. nov. (From braegen—Old English fo brain. The spore clusters have a brain-like appearance when observed with the SEM.) Should another strain be found, it is understood that the new species, which is the type strain, should also be the type subspecies. This is in accordance with the Rules of Nomenclature of Bacteria [Lapage, S. P., P. H. A. Sneath, E. F. Lessel, V. B. D. Skerman, H. P. R. Seeliger, and W. A. Clark, ed. 1975. International code of nomenclature of bacteria, 1976 Revision. Americal Society for Microbiology, Washington, D.C.].

TABLE 1

Color Characteristics* on Ektachrome[1,2]

| Agar Medium | Determination | S. braegensis NRRL 12567 | | S. vinaceus-drappus NRRL 2363 | |
|---|---|---|---|---|---|
| | | Chip | Color | Chip | Color |
| Bennett's | S | 7 | pale pink | 7 | pale pink |
| | R | 52 | light orange | 90 | grayish yellow |
| Czapek's | S | 233 | pale gray | 22 | reddish gray |
| sucrose | R | 31 | pale yellowish pink | 31 | pale yellowish pink |
| Maltose- | S | 233 | pale gray | 22 | reddish gray |
| tryptone | R | 52 | light orange | 90 | grayish yellow |
| Peptone- | S | 10 | pinkish gray | 10 | pinkish gray |
| iron | R | 87 | moderate yellow | 87 | moderate yellow |
| 0.1% Tyrosine | S | 233 | pale gray | 8 | grayish pink |
| | R | 31 | pale yellowish | 31 | dark yellowish |

TABLE 1-continued

| | | Color Characteristics* on Ektachrome[1,2] | | | |
|---|---|---|---|---|---|
| | Deter- | S. braegensis | | S. vinaceus-drappus | |
| | mina- | NRRL 12567 | | NRRL 2363 | |
| Agar Medium | tion | Chip | Color | Chip | Color |
| Casein starch | S | 233 | pink pale gray | 22 | pink reddish gray |
| | R | 31 | pale yellowish pink | 31 | pale yellowish pink |

S = Surface
R = Reverse

[1]Dietz, A. 1954. Ektachrome transparencies as aids in actinomycete classification. Ann. N.Y. Acad. Sci. 60:152–154.

[2]Dietz, A. and D. W. Thayer (ed.). 1980. Actinomycete Taxonomy (Procedures for Studying Aerobic Actinomycetes with Emphasis on the Streptomycetes). SIM Special Publication Number 6. Soc. for Ind. Microbiol., Arlington, VA.

*Growth on media in tubes was photographed after seven days incubation at 280°C. Color was determined by comparison with NBS color chips [SP 440. Color: Universal Language and Dictionary of Names. U.S. Government Printing Office, Washington, D.C. 20402.]; and [SRM 2106. ISCC-NBS Centroid Color Charts. Office of Standard Reference Material, Room 8311, Chem. Building, National Bureau of Standards, Washington, D.C. 20234].

TABLE 2

| | | Reference Color Characteristics* | | | |
|---|---|---|---|---|---|
| | Deter- | S. braegensis | | S. vinaceus-drappus | |
| | mina- | NRRL 12567 | | (NRRL 2363) | |
| Agar Medium | tion | Chip | Color | Chip | Color |
| Bennett's | S | 33 | brownish pink | 60 | light grayish brown |
| | R | 53 | moderate orange | 71 | moderate orange-yellow |
| | P | 53 | moderate orange | — | — |
| Czapek's sucrose | S | 79 | light grayish yellowish brown | 60 | light grayish brown |
| | R | 52 | light orange | 73 | pale orange yellow |
| | P | 33 | light pink | — | — |
| Maltose-tryptone | S | 80 | grayish yellowish brown | 63 | light brownish gray |
| | R | 53 | moderate orange | 70 | light orange yellow |
| | P | 71 | moderate orange yellow | 70 | light orange yellow |
| Yeast extract-malt extract (ISP-2) | S | 33 | brownish pink | 60 | light grayish brown |
| | R | 53 | moderate orange | 71 | moderate orange yellow |
| | P | 53 | moderate orange | — | — |
| Oatmeal (ISP-3) | S | 81 | dark grayish yellowish brown | 61 | grayish brown |
| | R | 73 | pale orange yellow | 58 | moderate brown |
| | P | 33 | brownish pink | — | — |
| Inorganic salts starch (ISP-4) | S | 65 | brownish black | 63 | light grayish brown |
| | R | 73 | pale orange yellow | 73 | pale orange yellow |
| | P | 53 | light orange | — | — |
| Glycerol-asparagine (ISP-5) | S | 80 | grayish yellowish brown | 63 | light grayish brown |
| | R | 52 | light orange | 70 | light orange yellow |
| | P | 70 | light orange yellow | 70 | light orange yellow |

S = Surface
R = Reverse
P = Pigment

*Color determination was made on growth on plates incubated 14 days at 28° C. Color was determined by comparison with NBS color chips [SP 440, supra] and [SRM 2106, supra].

TABLE 3

Growth on Carbon Compounds in the Synthetic Medium of Shirling and Gottlieb*

| Synthetic Medium (ISP-9) | S. braegensis NRRL 12567 | S. vinaceus-drappus (NRRL 2363) |
|---|---|---|
| Negative Control (No carbon cpd.) | ± | − |
| Positive Control (D-glucose) | + | + |

TABLE 3-continued

Growth on Carbon Compounds in the Synthetic Medium of Shirling and Gottlieb*

| Synthetic Medium (ISP-9) | S. braegensis NRRL 12567 | S. vinaceus-drappus (NRRL 2363) |
|---|---|---|
| L-arabinose | ± | ++ |
| Sucrose | ++ | ++ |
| D-xylose | + | ++ |
| Inositol | ++ | ++ |

TABLE 3-continued

Growth on Carbon Compounds in the Synthetic Medium of Shirling and Gottlieb*

| Synthetic Medium (ISP-9) | S. braegensis NRRL 12567 | S. vinaceus-drappus (NRRL 2363) |
|---|---|---|
| D-mannitol | ++ | ++ |
| D-fructose | + | ++ |
| Rhamnose | − | ++ |
| Raffinose | ++ | ++ |
| Cellulose | − | − |

++ = Strong utilization
+ = Positive utilization
± = Doubtful utilization
− = No utilization
*Shirling and Gottlieb, supra.

TABLE 4

Culture Characteristics - General

| Medium | Determination | S. braegensis NRRL 12567 | S. vinaceus-drappus (NRRL 2363) |
|---|---|---|---|
| Agar | | | |
| Peptone-iron | S | colorless vegetative growth | pale gray-pink |
| | R | light yellow-tan | yellow-tan |
| | P | — | — |
| | O | melanin-negative | melanin-negative |
| Calcium malate | S | very pale cream | pale gray-pink |
| | R | cream | pale gray-yellow |
| | P | — | — |
| | O | malate solubilized under growth | malate not solubilized |
| Glucose-asparagine | S | cream-white | pale gray-pink |
| | R | cream | pale yellow |
| | P | — | — |
| Skim milk | S | colorless vegetative center trace cream on edge | colorless to pale tan vegetative growth |
| | R | light yellow-tan-cream | orange |
| | P | yellow-tan | orange |
| | O | casein not solubilized | casein solubilized |
| Tyrosine | S | pale cream-white | gray |
| | R | yellow | orange-tan |
| | P | yellow | orange-tan |
| | O | tyrosine solubilized | tyrosine solubilized |
| Xanthine | S | pale cream-white | gray |
| | R | yellow | pale yellow-gray |
| | P | yellow | pale yellow |
| | O | xanthine solubilized under growth | xanthine solubilized |
| Nutrient starch | S | pale cream-white | gray |
| | R | yellow | olive |
| | P | pale yellow | — |
| | O | starch not solubilized | starch not solubilized |
| Yeast extract-malt extract | S | pale gray cream | gray cream |
| | R | pale maroon-tan | yellow-orange |
| | P | pale yellow-tan | pale yellow |
| Peptone-yeast extract-iron (ISP-6) | S | pale gray | colorless vegetative growth |
| | R | yellow | yellow-tan |
| | P | yellow | pale yellow-tan |
| | O | melanin negative | melanin negative |
| Tyrosine (ISP-7) | S | pale gray | pale gray |
| | R | pale maroon | cream gray |
| | P | — | — |
| | O | melanin negative | melanin negative |
| Broth | | | |
| Synthetic nitrate | S | — | pale peach aerial on surface ring and pellicle |
| | P | — | — |
| | O | compact bottom growth nitrates not reduced | flocculent bottom growth nitrates not reduced |
| Nutrient | S | — | white aerial on surface pellicle |
| | P | — | — |
| | O | compact bottom | flocculent bottom |
| Litmus milk | S | growth nitrates not reduced gray aerial on surface ring | growth nitrates not reduced trace gray aerial on cream-tan surface ring |
| | P | — | lavender |
| | O | no change pH 6.52 | litmus reduced slightly pH 6.2 |
| Gelatin | | | |
| Plain | S | gray aerial | trace gray aerial |
| | P | — | yellow-tan |
| | O | no liquefaction | trace to no liquefaction |
| Nutrient | S | gray aerial | — |
| | P | — | tan |
| | O | no liquefaction | trace liquefaction |

S = Surface (aerial growth unless otherwise noted)
R = Reverse
P = Pigment
O = Other characteristics The compound of the invention process is produced when the elaborating organism is grown in an aqueous nutrient medium under submerged conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously.

Production of the compound by the invention process can be effected at any temperature conductive to satisfactory growth of the microorganism, for example, between about 18° and 40° C., and preferably between about 20° and 28° C. Ordinarily, optimum production of the compound is obtained in about 2 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by adsorption on non-ionic macroporous resins. Ultrafiltration, cellulose chromatography (gradient elution) and gel permeation chromatography on G-25 Sephadex can be used to purify crude preparations of the antibiotic.

In a preferred recovery process, the compound produced by the subject process is recovered from the culture medium by separation of the mycelia and undissolved solids by conventional means, such as by filtration or centrifugation, and resin adsorption of the filtered broth. The antibiotic of the subject invention can be recovered from the filtered beer by resin sorption on a resin comprising a non-ionic macroporous copolymer of styrene cross-linked with divinylbenzene. Suitable resins are Amberlite XAD-2, XAD-4 and XAD-7, according to the procedure disclosed in U.S. Pat. No. 3,515,717. (Amberlite resins are avaliable from Rohm and Haas, Philadelphia, PA.). The antibiotic can be eluted from said resins by using acetone.

Resins other than XAD-2, XAD-4 and XAD-7 may be substituted. Charcoal can also be used. Extraction with a solvent like 1-butanol also can be used.

The eluting solvent from the resins will vary from resin to resin. In general, combinations of warer and a water-miscible solvent such as methanol, ethanol, tetrahydrofuran, diethylformamide or diethylsulfoxide are useful. The amount of organic solvent will vary from 2 to 90% (v/v).

Purification of the antibotic from the resin eluate can be done by the procedure listed above, i.e. ultrafiltration, cellulose chromatography, and gel permeation chromatography.

The presence of an acidic hydroxyl (S) group on antibiotic U-64,864 allows for the preparation of base addition salts, e.g. metal salts, for example, sodium, calcium, magnesium and potassium; and other salts, for example, ammonium and triethyl ammonium. These salts can be used for the same purposes as the parent antibiotic.

The following examples are illustrative of the process and product of the invention, but are not to be construed as limiting. All percentages are by weight and all solvent mixture proportions are by volume unless otherwise noted.

EXAMPLE 1

A. Fermentation

A biologically pure culture of *Streptomyces braegensis* Dietz sp.n. NRRL 12567, is used to inoculate 500-ml. Erlenmeyer pre-seed flasks containing 100 ml of sterile medium consisting of the following ingredients:

|  | g/liter |
| --- | --- |
| Black-strap molasses | 4.0 |
| Dextrin | 20.0 |
| Difco peptone | 10.0 |
| Difco yeast extract | 4.0 |
| Asparagine | 0.2 |
| $CoCl_2.6H_2O$ | .001 |
| Tap water q.s. to 1 liter | | pH adjusted to 7.2 with KOH before sterilization. Lard oil (1 ml/l) is added as an antifoaming agent.

The preseed inoculum is grown for three days at 28° C. on a Gump rotary shaker operating at 250 rpm and havin g a 2 ½ inch stroke.

Preseed inoculum (300 ml), prepared as described above, is used to inoculate a 20 l seed tank containing 20 l of sterile medium as used above.

The inoculated seed medium is incubated at a temperature of 28° C. for 2 days with agitation at 350 rpm and air sparged in at 8 l/min with a back pressure of 8 psig.

Seed inoculum (5% seed), prepared as described above, is used to inoculate a 250 l fermentation tank containing 250 l. of the following sterile medium:

|  | g/liter |
| --- | --- |
| Black-strap molasses | 10.0 |
| Corn starch | 25.0 |
| Dextrin | 5.0 |
| Brewers yeast | 2.0 |
| Kay soy (Supplied by Archer-Daniel Co.) | 13.0 |
| Cornsteep liquor | 8.0 |
| $KH_2PO_4$ | 3.0 |
| Mineral salt solution A* | 1 ml/l |
| Mineral salt solution B** | 1 ml/l |
| Lard oil | 0.5 ml/l |
| Tap water | |
| pH adjusted to 7.2 with $NH_4OH$ before sterilization. | |

| *Mineral Salt Solution A | g/100 ml |
| --- | --- |
| $MgSO_4.7H_2O$ | 5.0 |
| $MnSO_4.H_2O$ | 0.30 |
| $FeSO_4.7H_2O$ | 1.0 |
| $ZnSO_4.7H_2O$ | 0.30 |
| $CoCl_2.6H_2O$ | 0.10 |
| Distilled Water (about 90 ml) | |
| Adjust pH to 2.0 with dilute sulfuric acid | |
| Add distilled water to make 100 ml | |

| **Mineral Salt Solution B | g/100 ml |
| --- | --- |
| $KH_2PO_4$ | 5.0 |
| KCl | 10.0 |
| Use distilled water and make to volume. | |

The inoculated fermentation medium is incubated at a temperature of 28° C. for 5 days with agitation at 250 rpm and air sparged in at 250 l/min.

A typical five-day fermentation has the following titers of antibiotic in the fermentation broth:

| Day | Assay, *S. pyogenes* (zone size in mm) |
| --- | --- |
| 1 | 0 |
| 2 | 18 |
| 3 | 25 |
| 4 | 26 |
| 5 | 27.5 |

The assay is a *Streptococcus pyogenes* disc agar plate diffusion assay using 0.1 M phosphate buffer, pH 5.0 as diluent.

B. Recovery

To whole beer (ca. 9 l) from a fermentation, as described above, is added 1 liter of diatomaceous earth (dicalite) at harvest pH 7.6. This slurry is filtered over a bed of Dicalite 4200 with suction. The cake is washed with 1 liter of deionized water to give 11.5 liters of combined filtrate-wash.

Assay: Filtered beer = 23 mm (vs. *S. pyogenes*—zone site).

XAD-2 Sorption

The above filtrate-wash is passed over a column of XAD-2resin which measures 6×70 cm. The column is washed with 4 liters of deionized water and eluted with 4 liters each of 10% acetone in water (v/v), followed by 4 l of 25% acetone in water. Two-liter fractions are collected.

There is no activity in the spent or the wash fractions. The first three fractions (6 liter eluate) are dark and give zones of 26, 26 and 24 mm against *S. pyogenes*. The last 2 liter fraction gives a trace zone. Fractions 1–3 are pooled and stripped of acetone on a rotary evaporator. The aqueous can be lyophilized to give a solid preparation.

C. Purification

An aqueous concentrate, obtained as described above, is passed over a UM 10 ultrafilter until only 300 ml remain in the retentate (from 4.0 liters). The retentate is diluted to 2.0 liters and the filtration is repeated. Both UM10 filtrates are passed over a UM05 filter. The following table shows the results in sequence.

| Sample | Volume | BU/ml | Total BU | Solids | Specific Activity |
|---|---|---|---|---|---|
| UM10R | 1.0 L | 2 | 2,000 | 3.15 g | 0.63 BU/mg |
| UM05F | 5.0 L | 1 | 5,000 | 1.26 g | 4.0 BU/mg |
| UM05R | 450.0 ml | 20 | 9,000 | 5.5 g | 1.64 BU/mg |

Each of the above samples gives a biozone at Rf 0.3 with 1:1 methanol:water on Analtech silica gel plates.

A BU (biounit) is defined as the concentration of the antibiotic which gives a 20 mm zone of inhibition in the agar diffusion assay when 100 λ are loaded onto a 12.7 mm pad.

PM 30 and UM 10 filters are two of a series of filter membranes made by the Amicon Corp. (Lexington, MA. 02173). They belong to the Diaflo ® series and are used with stirred cells, also made by Amicon.

Silica Gel Chromatography

The UM05F sample above (1.26 g) is slurried in 25 ml of 1:1 methanol:water. About 10 g of silica gel is added and the solvents removed on a rotary evaporator. The dry sample-silica gel mixture is used to replace an equal amount of silica gel atop a 2.5×100 cm silica gel column which had been slurry-packed with 2:1 methanol:water (V/V). The LKB Ultrograd is used to generate a 16 hr gradient from 2:1 to 1:4 methanol:water. The tubes are assayed with *S. pyogenes* and scanned in the UV from 360–200nm. Tubes 115–150 are pooled on the basis of peak activity and absorbency at 290 nm (25 ml/tube). This is concetrated to give 330 mg of solids. This is freed of silica gel with XAD-2 sorption-desorption to give 166 mg of essentially pure antibiotic U-64,864.

We claim:

1. A biologically pure culture of the microorganism *Streptomyces braegensis* Dietz sp.n., having all of the identifying characteristics of NRRL 12567, said culture being capable of producing the antibiotic U-64,864 in a recoverable quantity upon fermentation in an aqueous nutrient medium containing assimilable sources of carbon, nitrogen and inorganic substances.

* * * * *